United States Patent
Hojo et al.

(10) Patent No.: US 10,182,566 B2
(45) Date of Patent: Jan. 22, 2019

(54) SUSTAINED RELEASE PHEROMONE PREPARATION OF VINE MEALYBUG AND CONTROL METHOD USING THE PREPARATION

(71) Applicant: Shin-Etsu Chemical Co., Ltd., Chiyoda-ku, Tokyo (JP)

(72) Inventors: Tatsuya Hojo, Joetsu (JP); Takeshi Kinsho, Joetsu (JP); Erina Ohno, Joetsu (JP); Miyoshi Yamashita, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/445,098

(22) Filed: Feb. 28, 2017

(65) Prior Publication Data

US 2017/0251667 A1    Sep. 7, 2017

(30) Foreign Application Priority Data

Mar. 3, 2016 (JP) ................................ 2016-041070
Dec. 5, 2016 (JP) ................................ 2016-235948

(51) Int. Cl.
| | | |
|---|---|---|
| *A01N 37/06* | (2006.01) | |
| *A01N 25/10* | (2006.01) | |
| *A01N 37/02* | (2006.01) | |
| *A01N 25/18* | (2006.01) | |

(52) U.S. Cl.
CPC ............ *A01N 37/06* (2013.01); *A01N 25/10* (2013.01); *A01N 25/18* (2013.01); *A01N 37/02* (2013.01)

(58) Field of Classification Search
CPC ......... A01N 25/10; A01N 37/02; A01N 37/10
See application file for complete search history.

(56) References Cited

U.S. PATENT DOCUMENTS 5,670,145 A * 9/1997 Wright ................. A01N 25/18
424/84

FOREIGN PATENT DOCUMENTS

| JP | 57-9705 A | 1/1982 |
|---|---|---|
| JP | 62-195303 A | 8/1987 |
| JP | 6-211614 A | 8/1994 |
| JP | 11-69936 A | 3/1999 |

OTHER PUBLICATIONS

European Search Report issued in counterpart European Application No. 17156964.3 dated Jul. 7, 2017 (13 pages).
Kol-Maimon et al., "Male behaviors reveal multiple pherotypes within vine mealybug *Planococcus ficus* (Signoret) (Hemiptera; Pseudococcidae) populations", Naturwissenschaften, Oct. 28, 2010, pp. 1047-1057, vol. 92, No. 12, Springer, Berlin, Germany, XP019863644.
Daradics et al., "Synthesis of 7(E), 9(Z)-Dodecadien-1-yl Acetate, the Sex Pheromone of European Grape Vine Moth *Lobesia botrana*, Involving Phase Transfer Technique", Journal Fuer Praktische Chemie, Jan. 1, 1987, pp. 457-461, vol. 329, No. 3, XP009043611.
Labovitz et al., "Synthesis of (7E, 9Z)—7, 9-Dodecadien-1-YL Acetate, A Sex Pheromone of Lobesia Botrana" Jan. 1, 1975, pp. 4209-4212, vol. 16, No. 48, XP055385696.

* cited by examiner

*Primary Examiner* — Zohreh A Fay
(74) *Attorney, Agent, or Firm* — Crowell & Moring LLP

(57) ABSTRACT

Provided are a sustained release pheromone preparation capable of maintaining a high amount of pheromone release throughout a control period of vine mealybug (VMB) having lavandulyl senecioate (LVSN) as a pheromone substance; and a control method with the preparation. More specifically, provided are a sustained release pheromone preparation comprising a first pheromone substance, and a first container having the first pheromone substance sealed therein and comprising a first polymer membrane made of an ethylene vinyl acetate copolymer containing vinyl acetate units of from 0.5 to 10% by weight, wherein the first pheromone substance is lavandulyl senecioate, which is a pheromone substance of vine mealybug, and the lavandulyl senecioate can be released into the air through the first polymer membrane for 150 days or more; and others.

8 Claims, 2 Drawing Sheets

SUSTAINED RELEASE PHEROMONE PREPARATION OF VINE MEALYBUG AND CONTROL METHOD USING THE PREPARATION

BACKGROUND OF THE INVENTION

1. Field of the Invention

The present invention relates to a sustained release pheromone preparation which releases a pheromone substance into the air for controlling vine mealybug (hereinafter also referred to as "VMB") having lavandulyl senecioate (hereinafter also referred to as "LVSN") as a pheromone substance through mass trapping or mating disruption and a control method using the preparation.

2. Description of the Related Art

What is important for establishing a control technology of making use of pheromone is sustained release of pheromone from an attracting source in an amount sufficient to attract wild insects with respect to the mass trapping, and is floating of pheromone in an amount sufficient to disrupt the mating in an entire field to be controlled with respect to the mating disruption. Since insect pests generally emerge over a long period of time from spring to autumn, the mass trapping and the mating disruption are made possible by sustained release of a pheromone substance from a sustained release pheromone preparation having the pheromone substance therein throughout the emergence period. Thus, the development of the sustained release pheromone preparation against a target insect pest has become very important for establishing a control technology with the use of pheromone.

A sustained release pheromone dispenser made of a polymer material such as polyethylene, polypropylene or an ethylene-vinyl acetate copolymer containing vinyl acetate units of 20% by weight or less (hereinafter also referred to as "EVA"), each having an average equilibrium swelling ratio at 20° C. of from 2 to 6% by weight, is known as a preparation for continuously releasing a predetermined amount of a pheromone substance for a long period of time (JP 62-195303A). It is also known that a container such as a cap, a small tube, a laminate bag or a capsule has a pheromone substance sealed therein, wherein the container is made of a material having a release-amount-controlling function, such as rubber, polyethylene, polypropylene, an ethylene-vinyl acetate copolymer containing ethylene units of 90% by weight or more, or polyvinyl chloride, where the ethylene units mean the repeating units derived from ethylene monomers (JP 11-069936A).

Among them, polyolefin-based plastics typified by polyethylene are present in various grades with different properties so that a range of their selection is wide and their cost is low because of their broad utility. Further, the polyolefin-based plastics also have excellent moldability, and allow various types of molding such as extrusion molding, film molding, stretching, and injection molding. In addition, due to excellent mechanical strength, particularly excellent mechanical strength at low temperatures, the polyolefin-based plastics are suited for use during a low temperature period or in a low temperature region.

Further, when a pheromone substance is an acetate compound of a linear aliphatic higher alcohol and the acetate compound has a carbon atom number of from 12 to 20 including a carbon atom number of its functional group, a sustained release pheromone preparation comprising a low-density polyethylene membrane allows the pheromone substance to be released from the preparation continuously for a long period of time. Such a preparation is therefore effective against insect pests that emerge for a long period of time (JP 57-009705A).

SUMMARY OF THE INVENTION

However, the sustained release pheromone preparations disclosed in JP 62-195303A and JP 11-069936A are ineffective against insect pests which emerge for a long period of time. It is because although the linear acetate compound having a carbon atom number of 12 to 20 including a carbon atom number of its functional group, which is a pheromone substance, has good compatibility with an ethylene-vinyl acetate copolymer membrane and a release amount of the substance can be increased, the release of the linear acetate compound ends in a short period of time.

The inventors thought on basis of finding in JP 57-009705A that a similar result would be obtained also from the use of LVSN. It is because the LVSN has a similar structure and has a carbon atom number of 15 including a carbon atom number of its functional group, although the LVSN is a monoterpene type alcohol having a tri-substituted double bond and a branch of an isopropenyl group. However, the inventors have found that although the acetate compound and LVSN are both ester compounds, they differ in permeation through a polyethylene film owing to the acetate compound having good compatibility or affinity with the polyethylene film, while the LVSN having poor compatibility or affinity with the polyethylene film.

With respect to the mass trapping or the mating disruption, it is necessary to maintain a high release amount from a sustained release pheromone preparation. Since the emergence period of VMB is known to be long from April to November in Italy, there is a demand for the development of a sustained release pheromone preparation capable of continuing release for a long period of time.

An object of the invention is to provide a sustained release pheromone preparation which can maintain a high amount of pheromone release against VMB having a pheromone substance of LVSN throughout the control period; and a control method using the preparation.

The inventors have found that contrary to the expectation that it is difficult to use an EVA membrane for LVSN having a carbon atom number of 15 including a carbon atom number of its functional group. EVA containing a predetermined amount of vinyl acetate units surprisingly makes it possible to release a predetermined amount of LVSN for a long period of time.

In one aspect of the invention, there is provided a sustained release pheromone preparation comprising a first pheromone substance, and a first container having the first pheromone substance sealed therein and comprising a first polymer membrane made of an ethylene-vinyl acetate copolymer containing vinyl acetate units of from 0.5 to 10% by weight, wherein the first pheromone substance is LVSN, which is a pheromone substance of VMB, and the LVSN can be released into the air through the first polymer membrane for 150 days or more.

In another aspect of the invention, there is provided a method of controlling VMB, comprising the step of: releasing, to a field, LVSN from the sustained release pheromone preparation.

In one of the embodiments, the sustained release pheromone preparation may further comprise a second pheromone substance, and at least one second container having the second pheromone substance sealed therein and comprising a second polymer membrane. When (E,Z)-7,9-dodecadienyl acetate, which is a pheromone substance of European grapevine moth, is used as the second pheromone substance, there can be provided a method of simultaneously controlling VMB and European grapevine moth, comprising the step of: releasing LVSN and (E,Z)-7,9-dodecadienyl acetate to a field from the sustained release pheromone preparation.

According to the invention, the sustained release pheromone preparation makes it possible to control VMB having LVSN as a pheromone substance for a period as long as 150 days or more and to suppress the damage by VMB of fruit trees such as grapes. In one of the embodiments, the sustained release pheromone preparation can control simultaneously, for example, VMB and European grapevine moth.

BRIEF DESCRIPTION OF THE DRAWINGS

FIG. 1 shows a production process of the sustained release pheromone preparation in accordance with the invention, in which

DETAILED DESCRIPTION OF THE PREFERRED EMBODIMENTS

Figure 1A:
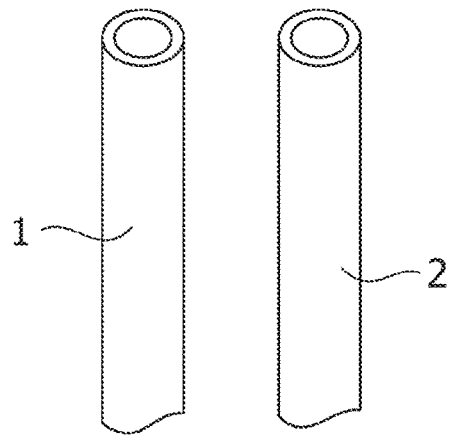
FIG. 1A shows the first container and the second container.

An insect pest targeted by the sustained release pheromone preparation is not particularly limited insofar as it is an insect pest having LVSN as a pheromone substance. Examples of the insect pest include insect pests belonging to the orders of Lepidoptera, Coleoptera, Hymemoptera, and Hemiptera. More specifically, the insect pest to be targeted is, for example, vine mealybug (*Planococcus ficus*).

LVSN is a pheromone substance of an insect pest to be controlled. The pheromone substance is not limited to a compound extracted actually from the insect pest and includes the industrially synthesized same compound. The LVSN is preferably the synthesized compound from the standpoint of economy. Although stereoisomers are present as the LVSN, they are not particularly limited. For example, the LVSN may be an S isomer, an R isomer, or a mixture of S and R isomers including a racemate. The LVSN may contain impurities generated inevitably during the production thereof.

The sustained release pheromone preparation may comprise, in addition to the LVSN, a physiologically active substance acting on another individual of the same species, and/or an additive such as a diluent, a polymerization inhibitor, an anti-oxidant and an ultraviolet absorber, the additive not affecting the physiological action of the insect pest of interest. Although the amount of each additive is variable depending on, for example, the environment in which the preparation is used, it is preferably from 0.1 to 5.0% by weight relative to the total weight of the mixture of LVSN and the additive.

Examples of the physiologically active substance acting on another individual of the same species include lavandulol and lavandulyl isovalerate. The term "another individual of the same species" means the individual having a reaction to lavandulol, lavandulyl isovalerate or the like, but not releasing the lavandulol, lavandulyl isovalerate or the like. Although stereoisomers are present as the lavandulol, lavandulyl isovalerate or the like, they are not particularly limited. For example, the lavandulol, lavandulyl isovalerate or the like may be an S isomer, an R isomer, or a mixture of S and R isomers including a racemate.

Examples of the diluent include dodecyl acetate, tetradecyl acetate, hexadecyl acetate, 1-dodecanoic, 1-tetradecanol and 1-hexadecanol.

Examples of the polymerization inhibitor include 2,6-di-tert-butyl-4-methylphenol and 2,2'-methylenebis(4-methyl-6-t-butylphenol).

Examples of the anti-oxidant include butylhydroxytoluene, butylhydroxyanisole, hydroquinone and Vitamin E.

Examples of the ultraviolet absorber include 2-hydroxy-4-octoxybenzophenone, 2-(2'-hydroxy-3'-tert-butyl-5'-methylphenyl)-5-chlorobenzotriazole and 2,5'-di-t-butylhydroquinone.

The sustained release pheromone preparation comprises LVSN (first pheromone substance), and a first container having the LVSN sealed therein and comprising an EVA membrane which is an LVSN-permeable polymer membrane (first polymer membrane).

The EVA contains vinyl acetate units, which are repeating units derived from vinyl acetate monomers, of from 0.5 to 10% by weight, preferably from 0.5 to 6% by weight, more preferably from 0.5 to 3% by weight. EVA containing vinyl acetate units of less than 0.5% by weight cannot attain a proper release rate, because the permeation rate of the pheromone substance through an EVA membrane is slow even with the thickness of the membrane reduced. On the other hand, EVA containing vinyl acetate units of more than 10% by weight cannot be processed into the preparation because of reduced rigidity of the EVA.

The molecular weight of the EVA is not particularly limited. The weight-average molecular weight (Mw) measured by gel permeation chromatography (GPC) with polystyrene standard is preferably from 50,000 to 500,000 from the standpoint of release performance and processability.

The sustained release pheromone preparation may comprise, in addition to the first container, a second pheromone substance, and at least one second container having the second pheromone substance sealed therein and comprising a second polymer membrane.

Examples of insect pests having the second pheromone substance to be sealed in the second container include insect pests belonging to the orders of Hemiptera, Lepidoptera, Coleoptera, and Hymemoptera.

Examples of insect pests belonging to the order of Hemiptera include, in addition to VMB, those of the genus *Halyomorpha* such as *Halyomorpha hales*, and those of the family Cicadellidae such as *Erythroneura ziczac*.

Examples of insect pests belonging to the order of Lepidoptera include those of the genus *Argyrotaenia* such as European grapevine moth (*Lobesia, botrana*, hereinafter also referred to as "EGVM"), European grape berry moth (*Eupoecilia ambiguella*, hereinafter referred to as "EGBM"), *Argyrotaenia liungiana, Argyrotaenia citrana, Argyrotaenia politana, Argyrotaenia pulchellana, Argyrotaenia sphaleropa, Argyrotaenia tabulana*, and *Argyrotaenia velutinana* and honeydew moth (*Cryptoblabes gnidiella*).

Examples of insect pests belonging to the order of Coleoptera include those of the family Scarabaeidae such as *Pelidnota punctata*, and those of the family Glaphyridae such as *Typhaeus typhoeus*.

Examples of insect pests belonging to the order of Hymemoptera include those of the family Braconidae such as *Dolichogenidae tasmanica*, those of the family Alphelinidae such as *Aphis illinoisensis*, and those of the family Encyrtidae such as *Anagyrus dactylopii*.

The second pheromone substance to be sealed in the second container is not particularly limited insofar as it is a physiologically active substance which promotes a certain behavior or growth change of individuals. Examples of the second pheromone substance include sex pheromone, trail pheromone, aggregation pheromone, and alarm pheromone.

Examples of the sex pheromone include, in addition to the LVSN, an aliphatic acetate having a carbon atom number of from 12 to 20 including a carbon atom number of its functional group (i.e. in the total number of carbon atoms) and an aliphatic aldehyde having a carbon atom number of from 12 to 20 including a carbon atom number of its functional group (i.e. in the total number of carbon atoms).

Examples of the aliphatic acetate having a carbon atom number of from 12 to 20 including a carbon atom number of its functional group include (E,Z)-7,9-dodecadienyl acetate (hereinafter also referred to as "(E,Z)-7,9-DDDA"), which is a pheromone substance of EGVM; (Z)-9-dodecenyl acetate, (E)-9-dodecenyl acetate and (Z)-9-tetradecenyl acetate, which are pheromone substances of EGBM; and (Z)-11-tetradecenyl acetate, which is a pheromone substance of *Argyrotaenia pulchellana*.

Examples of the aliphatic aldehyde having a carbon atom number of from 12 to 20 including a carbon atom number of its functional group include (Z)-11-hexadecenal, (E)-11-hexadecenal, (Z)-13-octadecenal and (E)-13-octadecenal, which are pheromone substances of a honeydew moth.

Examples of the trail pheromone include (Z)-9-hexadecenal. Examples of the aggregation pheromone include 2,3-hexanediol. Examples of the alarm pheromone include 2-heptanone and isopentyl acetate.

The pheromone substance is not limited to compounds extracted actually from insect pests and includes the industrially synthesized same compound. The pheromone substrate is preferably the synthesized compound from the standpoint of economy.

The pheromone substance may contain geometric isomers. When the pheromone substance is (E,Z)-7,9-DDDA, it may be an (E,E) isomer, a (Z,E) isomer, a (Z,Z) isomer or a mixture thereof.

The pheromone substance may be used in combination of two or more.

The second pheromone substance to be sealed in the second container may contain, similarly to the above-described LVSV, impurities generated inevitably during the production thereof. Similarly to the first pheromone substance, the second pheromone substance may contain a physiologically active substance acting on another individual of the same species, and/or an additive such as a diluent, a polymerization inhibitor, an anti-oxidant and ultraviolet absorber, the additive not affecting the physiological action of insect pests having the second pheromone substance. Examples of the diluent, the polymerization inhibitor, the anti-oxidant and the ultraviolet absorber are the same as those described above with respect to the first pheromone substance.

The second polymer membrane of the second container is not particularly limited insofar as it allows the second pheromone substance to permeate therethrough and to be released for a long period of time. Examples of the second polymer membrane include the membranes of ethylene vinyl acetate copolymers, polyolefins, vinyl-based polymers, polyesters, and biodegradable polymers. Examples of the polyolefins include polyethylene and polypropylene. Examples of the vinyl-based polymers include polyvinyl chloride. Examples of the polyesters include polyethylene terephthalate. Examples of the biodegradable polymers include condensation polymers between at least one dicarboxylic acid selected from the group consisting of oxalic acid, malonic acid, succinic acid, glutaric acid, adipic acid, sebacic acid, fumaric acid and maleic acid, and at least one polyol selected from the group consisting of ethylene glycol, propylene glycol, butanediol, pentanediol, hexanediol, octanediol and decanediol; a condensation polymer formed from at least one selected from the group consisting of lactic acid, hydroxyvaleric acid, hydroxycaproic acid and hydroxycapric acid; and aliphatic polyester-based thermoplastics such as polycaprolactone obtained by ring opening polymerization of ε-caprolactone. More specific examples of the biodegradable polymer include polylactic acid, polycaprolactone and polybutylene succinate adipate.

For example, when the second pheromone substance to be sealed in the second container is LVSN, the second polymer membrane is preferably the membrane of the above-described specific ethylene-vinyl acetate copolymer. The release period of 150 days or more can be expected from the membrane of the ethylene-vinyl acetate copolymer. When the second pheromone substance to be sealed in the second container is (E,Z)-7,9-DDDA, the second polymer membrane is preferably the membrane of polyethylene. The release period of 150 days or more can be expected from the membrane of polyethylene.

When the membranes of the first and second containers of the sustained release pheromone preparation are made of LVSN-permeable EVA, the LVSN can be released through the membranes to the outside such as a field. The entirety of the first and second containers of the sustained release pheromone preparation may be made of the EVA membrane. Alternatively, a part or parts of the first and second containers such as wall or walls may be made of the EVA membrane. When the first and second containers partially comprise the EVA membrane, the LVSN can be released from the membrane. When the first and second containers also partially comprise, for example, a polyethylene membrane, a pheromone substance other than the LVSN can be released simultaneously from the polyethylene membrane other than the EVA membrane with respect to the first and second containers.

Each of the first and second containers is preferably in form of a tube, a capsule, an ampule or a bottle. In particular, a tube type of container preferably has an inside diameter of from 0.5 to 2.5 mm, a surface area of from 600 to 4000 $mm^2$, and a membrane thickness of from 0.3 to 0.8 mm from the standpoint of uniform release. The container other than the tube type of container has a membrane thickness of preferably from 0.01 to 0.1 mm from the standpoint of easy handling because a thickened membrane has increased rigidity.

Each of the first and second containers may be in different form. However, each of the first and second containers is preferably in the same form from the standpoint of processability.

Each of the first and second containers contains a pheromone substance of preferably from 20 to 2000 mg, more preferably from 50 to 500 mg.

The polymer material formed into the polymer membranes of the first and second containers may contain an anti-oxidant, an ultraviolet absorber or the like to prevent the polymer material from getting deteriorated.

Examples of the anti-oxidant include phenol-based anti-oxidants such as ethylenebis(oxyethylene)bis(3-(5-tert-butyl-4-hydroxy-m-tolyl)propionate) and octadecyl-3-(3,5-di-tert-butyl-4-hydroxyphenyl)propionate; sulfur-based anti-oxidants such as didodecyl 3,3'-thiodipropionate; and phosphor-based anti-oxidants such as tris(2,4-di-tert-butylphenyl)phosphite.

Examples of the ultraviolet absorber include benzotriazole-based ultraviolet absorbers such as 2-(2'-hydroxy-3'-tert-butyl-5'-methylphenyl)-5-chlorobenzotriazole, and benzophenone-based ultraviolet absorbers such as 2-hydroxy-4-octoxybenzophenome.

The polymer material may contain the antioxidant and the ultraviolet absorber in each amount of preferably more than 0% by weight but not more than 3% by weight, more preferably more than 0% by weight but not more than 1% by weight, relative to the weight of the polymer material.

The polymer material may further contain an inorganic colorant such as iron oxide, chromium oxide, titanium oxide or carbon black; or an organic colorant such as a polycyclic pigment or azo-based pigment in a total amount of preferably more than 0% by weight but not more than 3% by weight, more preferably more than 0% by weight but not more than 1% by weight, relative to the weight of the polymer material from the standpoint of preventing ultraviolet-light deterioration of the LVSN.

To enhance processability, the polymer material may further contain an anti-blocking agent such as a metal salt of higher fatty acid, or an inorganic powder; or a lubricant such as a hydrocarbon, an alcohol, a higher fatty acid, an ester, a polyhydric alcohol partial ester, a metal salt of higher fatty acid, a natural wax, or a fatty acid amide in each amount of preferably more than 0% by weight but not more than 3% by weight, more preferably more than 0% by weight but not more than 1% by weight, relative to the weight of the polymer material.

The sustained release pheromone preparation may comprise a third container or more of the same kind or kinds as or different kind or kinds from that of the first or second container.

Figure 1B:
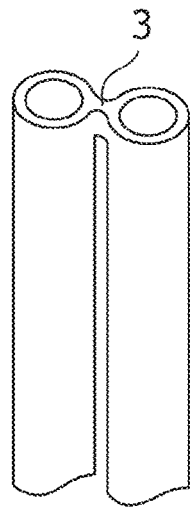
FIG. 1B shows a joint portion formed.
Figure 1C:
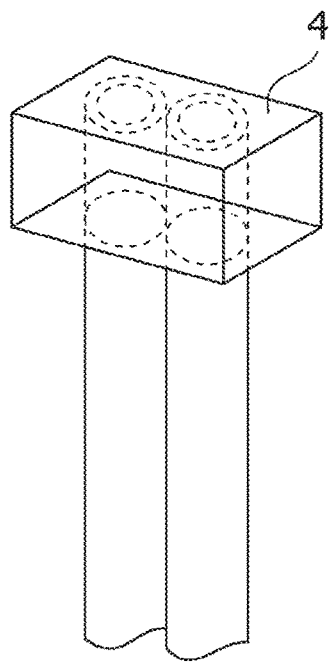
FIG. 1C shows a sealing step with a heat sealer.
Figure 1D:
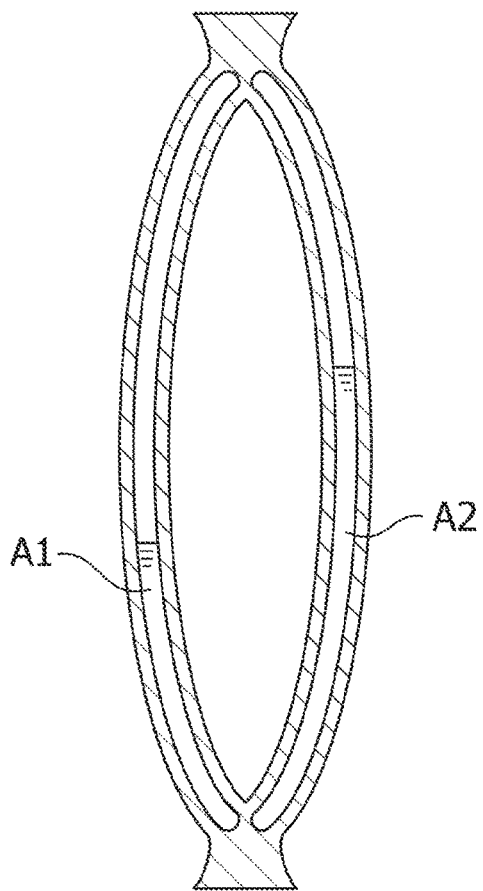
FIG. 1D is a cross-sectional view of the sustained release pheromone preparation.

A method of joining the first and second containers is not particularly limited. Examples thereof include a heat sealing method in which they are welded by heat; a two-color extrusion method in which polymer materials of different kinds are molded and joined simultaneously; and a chemical joining method with an adhesive or the like. The two-color extrusion method is preferred because it can simultaneously join the first and second containers during production of the containers and does not require a step of joining after production of the first and second containers. The first and second containers may be joined physically, for example, with a tape or a wire. During joining, a first container 1 and a second container 2 may be independent from each other as shown in FIG. 1A, or may be attached in parallel into one body at a joint 3 as shown in FIG. 1B. By chemically or physically joining the ends of the first and second containers with a heat sealer 4 as shown in FIG. 1C, a sustained release pheromone preparation containing pheromone substances A1 and A2 therein may be formed as shown in the cross-sectional view of FIG. 1D. The shape of the preparation is not limited to those in FIG. 1.

Figure 2:
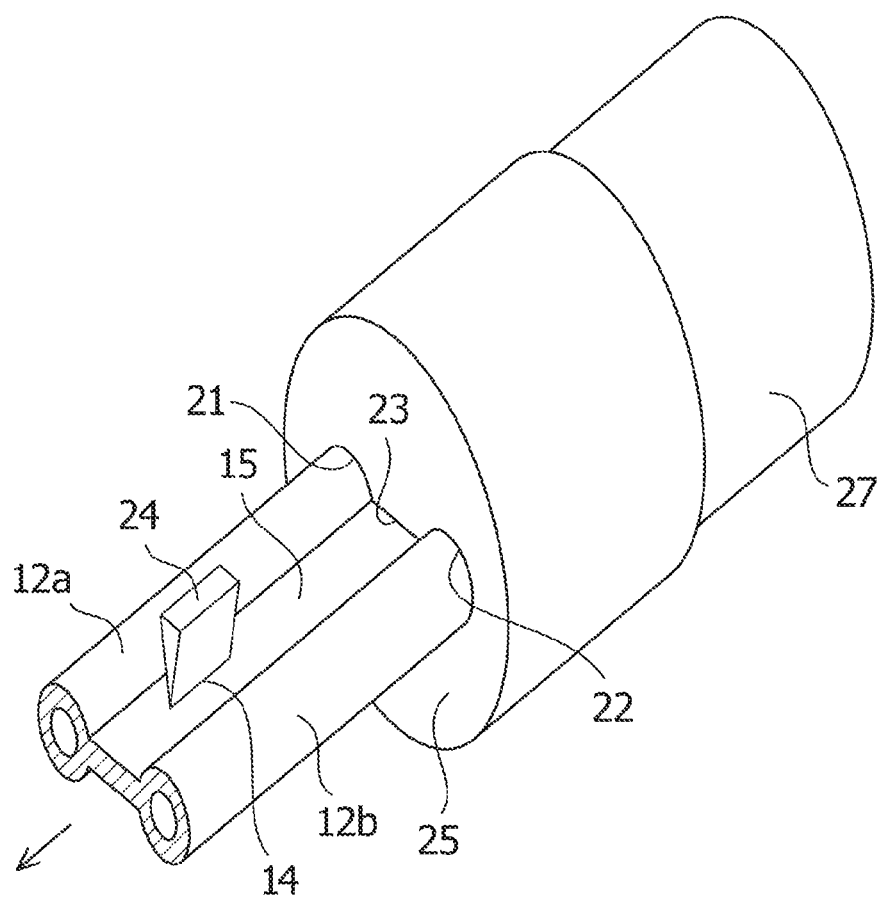
FIG. 2 shows a two-color extrusion method to produce the sustained release pheromone preparation in accordance with the invention.

The two-color extrusion method is not particularly limited. For example, it is preferable to perform the extrusion successively using a container manufacturing apparatus as partially shown in FIG. 2, comprising a cylinder 27 and an extrusion die 25 being attached to the cylinder 27 and having core-containing holes 21 and 22 with diameters equal to or different from each other in each diameter range of from 0.1 to 10.0 mm. When the polymer membrane of the first container 12a is made of EVA and the polymer membrane of the second container 12b is made of polyethylene, an EVA resin melted at the temperature of, for example, from 130 to 220° C. is extruded from the core-containing hole 21 of the extrusion die 25, while a polyethylene resin melted at the temperature of, for example, from 160 to 300° C. is extruded from the core-containing hole 22, so that the first container 12a and the second container 12b having different kinds of polymer membranes can be formed continuously and simultaneously. The first container 12a and the second container 12b just after extruded from the extrusion die 25 are still in a molten state so that they can be joined to each other by adjusting the distance between the core-containing holes 21 and 22 of the extrusion die 25 to fall within a range of from 0 to 5 mm. Alternatively, by making use of an extrusion die 25 in which two core-containing holes 21 and 22 are connected via a linear pore 23 having a length of from 0 to 10 mm, an EVA resin melted at the temperature of, for example, from 160 to 300° C. is extruded from the core-containing hole 21, while a polyethylene resin melted at the temperature of, for example, from 130 to 220° C. is extruded from the core-containing hole 22, so that the first container 12a and the second container 12b having polymer membranes of different kinds and being joined via a web 15 can be obtained. The web 15 may be optionally cut by a blade 24 to have a notch 14 or perforations so that the tubes joined at the joint 3 may also be obtained by opening the web 15.

The sustained release pheromone preparation can be obtained by sealing the pheromone substance or substances in liquid form in the first and second containers obtained by blow molding, extrusion molding or the like. The pheromone substance or substances in liquid form may be sealed in one or both of the containers by feeding the pheromone substance or substances through the same route as used for pushing out the air simultaneously with molding or extrusion molding.

In the above-described two-color extrusion method, for example, extrusion may be carried out while feeding each pheromone substance into each core of the core-containing holes 21 and 22. The extrusion temperature can be selected, depending on the boiling point or the like of each pheromone substance.

In insect pest control, a method of releasing a pheromone substance into the air is not limited insofar as it can result in mating disruption. It is preferable to use a sustained release preparation in form of a tube, a capsule, an ampoule or a bottle, each being filled with a pheromone substance, so as to allow the substance to permeate through the first and second containers.

Release control from the sustained release pheromone preparation targeting a single insect pest can often be achieved relatively easily because the pheromone substance used is a single substance or a mixture of compounds having similar chemical structures. In general, however, single insect pest fauna is very rare in a certain crop and in most cases, a plurality of insect pests having compounds of different chemical structures as pheromone substances are required to be controlled simultaneously. Thus, for simultaneous control of VMB and another insect pest, a pheromone substance excluding the LVSN and targeting the another insect pest is preferably sealed in the second container. For example, when VMB and EGVM are controlled simultaneously, the pheromone substance to be sealed in the second container is preferably (E,Z)-7,9-DDDA. In this example, a portion of the (E,Z)-7,9-DDDA may be sealed, together with LVSN, in the first container.

The release positions may be distributed uniformly in the field where the mating disruption is carried out and they are provided preferably from 1 to 2000 positions/ha, more preferably from 1 to 1000 positions/ha.

The release amount from one release position differs depending on the field environment, weather conditions or the like, and cannot be selected without reservation. The amount is not particularly limited insofar as it enables uniform floating in the field. The release amount is preferably from 0.5 to 4000 mg/day/position, more preferably, from 0.5 to 1000 mg/day/position.

EXAMPLES

Examples and Comparative Examples of the invention will hereinafter be described in detail. It should not be construed that the invention is limited to or by them.

Example 1

A tube made of EVA containing 0.5% by weight of vinyl acetate units and having an inside diameter of 1.2 mm and a thickness (membrane thickness) of 0.3 mm was formed as a first container by extrusion at a processing temperature of from 150 to 200° C.

BHT (2,6-di-tert-butyl-4-methylphenol) and HBMCBT (2-(2'-hydroxy-3'-tert-butyl-5'-methylphenyl)-5-chlorobenzotriazole) as stabilizers were added to 200 mg of LVSN to form a mixture, so that each concentration of the BHT and the HBMCBT in the mixture was 2% by weight. The mixture was poured into the tube as the first container, from one end of the tube. The liquid was sealed therein by applying a pressure to both ends while performing high-frequency heating. The tube was cut in the welded parts to obtain a sustained-release pheromone preparation having a length of 20 cm.

The sustained release pheromone preparations were placed in a temperature-controlled bath kept at a wind velocity of 1.0 msec and a temperature of 25° C. and a release rate from each preparation was measured for 180 days. The results are shown in Table 1.

Examples 2 to 4

Sustained-release pheromone preparations were produced and their release rates were measured in the same manner as in Example 1 except for the use of a tube obtained by extrusion of EVA containing 3% by weight of vinyl acetate units in Example 2, a tube obtained by extrusion of EVA containing 6% by weight of vinyl acetate units in Example 3, and a tube obtained by extrusion of EVA containing 10% by weight of vinyl acetate units in Example 4, each tube having an inside diameter of 1.2 mm and a membrane thickness of 0.3 mm. The results are shown in Table 1.

Examples 5 and 6

Sustained-release pheromone preparations were produced and their release rate was measured in the same manner as in Example 1 except for the use of, as the first container, a tube obtained by extrusion of EVA containing 3% by weight of vinyl acetate units and having an inside diameter of 1.2 mm and a membrane thickness of 0.5 mm in Example 5, and a tube obtained by extrusion of EVA containing 3% by weight of vinyl acetate units and having an inside diameter of 1.2 mm and a membrane thickness of 0.8 mm in Example 6. The results are shown in Table 1.

Comparative Example 1

A sustained-release pheromone preparation was produced and its release rate was measured in the same manner as in Example 1 except for the use of, as the first container, a tube obtained by extrusion of high-density polyethylene (HDPE) at a processing temperature of 250° C. and having an inside diameter of 1.2 mm and a membrane thickness of 0.3 mm. The results are shown in Table 1.

Example 1

| | first container (tube) | | | release rate (mg/day/preparation) | | |
|---|---|---|---|---|---|---|
| | inside diameter (mm) | membrane thickness (mm) | content of vinyl acetate units (% by weight) | 60 days later | 120 days later | 180 days later |
| Example 1 | 1.2 | 0.3 | 0.5 | 0.5 | 0.7 | 0.7 |
| Example 2 | 1.2 | 0.3 | 3 | 2.0 | 0.8 | 0.6 |
| Example 3 | 1.2 | 0.3 | 6 | 2.2 | 0.7 | 0.4 |
| Example 4 | 1.2 | 0.3 | 10 | 2.5 | 0.6 | 0.3 |
| Example 5 | 1.2 | 0.5 | 3 | 1.7 | 1.1 | 0.6 |
| Example 6 | 1.2 | 0.8 | 3 | 1.4 | 1.2 | 0.6 |
| Comp. Ex 1 | 1.2 | 0.3 | 0 | 0.03 | 0.08 | 0.08 |

The sustained-release pheromone preparation of the high-density polyethylene containing 0% by weight of vinyl acetate units hardly released the LVSN. However, the release rate increased as the vinyl acetate content in the polymer increased, it is considered that the LVSN hardly permeates through the polyethylene so that the release amount from the preparation is small, while EVA containing vinyl acetate units facilitates permeation of the LVSN through the membrane of the preparation so that the release amount increases.

Example 7 and Comparative Example 2

A tube made of EVA containing 3% by weight of vinyl acetate units and having an inside diameter of 1.2 mm and a thickness (membrane thickness) of 0.5 mm was formed as a first container by extrusion at a processing temperature of from 150 to 200° C.

BHT (2,6-di-tert-butyl-4-methylphenol) and HBMCBT {2-(2'-hydroxy-3'-tert-butyl-5'-methylphenyl)-5-chlorobenzotriazole} as stabilizers were added to 200 mg of LVSN to form a mixture, so that each concentration of the BHT and the HBMCBT in the mixture was 2% by weight. The mixture was poured into the tube as the first container, from one end thereof. The liquid was sealed therein by applying a pressure to both ends while high-frequency heating. The tube was cut in welded parts to obtain a sustained-release pheromone preparation having a length of 20 cm.

The sustained-release pheromone preparations, each having a sex pheromone substance of VMB added, were placed at 500 tubes/ha in a vineyard in Tuscany in Italy on April 18 in Example 7. The sustained release pheromone preparations were placed separately with equal intervals to release a necessary amount of the sex pheromone substance in Plot 1 where insect pests were controlled. As a result, a ratio of grape bunches damaged by the third generation, which was measured on September 3, are shown in Table 2.

A damaged bunch ratio in Plot 2, where no sustained-release pheromone preparation was placed, was also measured in Comparative Example 2.

It should be noted that the term "damaged bunch ratio" is used for estimating a mating disruption effect. Particularly in grapes, the damaged bunch ratio represented by the formula:

{(number of damaged bunches)/(number of bunches checked)}×100 is used as one of estimate criteria.

TABLE 2

|  | plot | damaged bunch ratio (%) |
|---|---|---|
| Example 7 | Plot 1 | 7 |
| Comp. Ex. 2 | Plot 2 | 25 |

In Example 7, VMB was controlled with the sustained release pheromone preparation having the pheromone substance of VMB added, and as a result, an average damaged bunch ratio by VMB was as good as 7%. In Comparative Example 2, VMB was controlled without a sustained release pheromone preparation having the pheromone substance of VMB added, and as a result, an average damaged bunch ratio by VMB was as high as 25%.

Example 8

A tube manufacturing apparatus comprised an extrusion die (corresponding to 25 in FIG. 2) having a hole obtained by joining two core-containing holes (corresponding to 21 and 22 in FIG. 2) each having a diameter of 5 mm via a linear hole (corresponding to 23 in FIG. 2) having a length of 10 mm. A coupled tube in which a first tube, as a first container, being made of EVA containing 0.5% by weight of vinyl acetate its and having an inside diameter of 1.2 mm and a thickness (membrane thickness) of 0.3 mm and a second tube, as a second container, being made of polyethylene and having an inside diameter of 1.4 mm and a thickness (membrane thickness) of 0.4 mm were coupled to each other, was produced by two-color extrusion with the apparatus. The two-color extrusion was carried out in such a manner that the EVA resin melted at 180° C. was extruded from one of the core-containing holes, while the polyethylene resin melted at 250° C. was extruded from the other of the core-containing holes.

BHT (2,6-di-tert-butyl-4-methylphenol) and HBMCBT (2-(2'-hydroxy-3'-tert-butyl-5'-methylphenyl)-5-chlorobenzotriazole) as stabilizers were added to 200 mg of LVSN to form a mixture, so that each concentration of the BHT and the HBMCBT in the mixture was 2% by weight. The mixture was poured into the first tube from one end thereof. Separately, BHT (2,6-di-tert-butyl-4-methylphenol) and HBMCBT (2-(2'-hydroxy-3'-tert-butyl-5'-methylphenyl)-5-chlorobenzotriazole) as stabilizers were added to 260 mg of (E,Z)-7,9-dodecadienyl acetate to form a mixture, so that each concentration of the BHT and the HBMCBT in the mixture was 2% by weight. The mixture was poured into the second tube from one end thereof. The liquids were sealed in the first tube and the second tube of the coupled tube, respectively, by applying a pressure to both ends of the coupled tube while performing high-frequency heating. The coupled tube was cut in the welded parts to obtain a sustained-release pheromone preparation having a length of 20 cm.

The sustained release pheromone preparations were placed in a temperature-controlled bath kept at a wind velocity of 1.0 m/sec and a temperature of 25° C. and a release rate from each preparation was measured for 180 days. The results are shown in Table 3.

Examples 9 and 10

Sustained-release pheromone preparations were obtained and their release rates were measured in the same manner as in Example 8 except that the first tube being made of EVA containing 3% by weight of vinyl acetate units and having an inside diameter of 1.2 mm and a membrane thickness of 0.3 mm in Example 9, and the first tube being made of EVA containing 10% by weight of vinyl acetate units and having an inside diameter of 1.2 mm and a membrane thickness of 0.3 mm in Example 10 were respectively produced by the two-color extrusion. The results are shown in Table 3.

Examples 11 and 12

Sustained-release pheromone preparations were obtained and their release rates were measured in the same manner as in Example 8 except that the first tube being made of EVA containing 3% by weight of vinyl acetate units and having an inside diameter of 1.2 mm and a membrane thickness of 0.5 mm in Example 11, and the first tube being made of EVA containing 3% by weight of vinyl acetate units and having an inside diameter of 1.2 mm and a membrane thickness of 0.8 mm in Example 12 were respectively produced by the two-color extrusion. The results are shown in Table 3.

Comparative Example 3

Sustained-release pheromone preparations were obtained and their release rates were measured in the same manner as in Example 8 except that a coupled tube in which the first tube being made of polyethylene and having an inside diameter of 1.2 mm and a membrane thickness of 0.3 mm and the second tube being made also of polyethylene and having an inside diameter of 1.4 mm and a thickness (membrane thickness) of 0.4 mm were coupled to each other, was produced by the extrusion. The results are shown in Table 3.

TABLE 3

| | first container (first tube) | | | release rate (mg/day/preparation) | | | second container (second tube) | | | release rate (mg/day/preparation) | | |
|---|---|---|---|---|---|---|---|---|---|---|---|---|
| | inside diameter (mm) | membrane thickness (mm) | content of vinyl acetate Units (wt %) | 60 days later | 120 days later | 180 days later | inside diameter (mm) | membrane thickness (mm) | content of polyethylene units (wt %) | 60 days later | 120 days later | 180 days later |
| Example 8 | 1.2 | 0.3 | 0.5 | 0.5 | 0.7 | 0.7 | 1.4 | 0.4 | 100 | 1.5 | 1.1 | 0.6 |
| Example 9 | 1.2 | 0.3 | 3 | 1.6 | 1.0 | 0.6 | 1.4 | 0.4 | 100 | 1.5 | 1.1 | 0.6 |
| Example 10 | 1.2 | 0.3 | 10 | 2.5 | 0.6 | 0.3 | 1.4 | 0.4 | 100 | 1.5 | 1.1 | 0.6 |
| Example 11 | 1.2 | 0.5 | 3 | 2.1 | 0.8 | 0.6 | 1.4 | 0.4 | 100 | 1.5 | 1.1 | 0.6 |
| Example 12 | 1.2 | 0.8 | 3 | 1.7 | 1.1 | 0.6 | 1.4 | 0.4 | 100 | 1.5 | 1.1 | 0.6 |
| Comp. Ex. 3 | 1.2 | 0.3 | 0 | 0.03 | 0.08 | 0.08 | 1.4 | 0.4 | 100 | 1.5 | 1.1 | 0.6 |

Examples 13 and Comparative Example 4

A tube manufacturing apparatus comprised an extrusion die (corresponding to 25 in FIG. 2) having a hole obtained by joining two core-containing holes (corresponding to 21 and 22 in FIG. 2) each having a diameter of 5 mm via a linear hole (corresponding to 23 in FIG. 2) having a length of 10 mm. A coupled tube in which a first tube, as a first container, being made of EVA containing 1% by weight of vinyl acetate units and having an inside diameter of 1.2 mm and a thickness (membrane thickness) of 0.5 mm and a second tube, as a second container, being made of polyethylene and having an inside diameter of 1.4 mm and a thickness (membrane thickness) of 0.4 mm were coupled to each other, was produced by two-color extrusion with the apparatus. The two-color extrusion was carried out in such a manner that the EVA resin melted at 180° C. was extruded from one of the core-containing holes, while the polyethylene resin melted at 250° C. was extruded from the other of the core-containing holes.

BHT (2,6-di-tert-butyl-4-methylphenol) and HBMCBT (2-(2'-hydroxy-3'-tert-butyl-5'-methylphenyl)-5-chlorobenzotriazole) as stabilizers were added to 200 mg of LVSN to form a mixture, so that each concentration of the BHT and the HBMCBT in the mixture was 2% by weight. The mixture was poured into the first tube from one end thereof. Separately, BHT (2,6-di-tert-butyl-4-methylphenol) and HBMCBT (2-(2'-hydroxy-3'-tert-butyl-5'-methylphenyl)-5-chlorobenzotriazole) as stabilizers were added to 260 mg of (E,Z)-7,9-dodecadienyl acetate to form a mixture, so that each concentration of the BHT and the HBMCBT in the mixture was 2% by weight. The mixture was poured into the second tube from one end thereof. The liquids were sealed in the first tube and the second tube of the coupled tube, respectively, by applying a pressure to both ends of the coupled tube while performing high-frequency heating. The coupled tube was cut in the welded parts to obtain a sustained-release pheromone preparation having a length of 20 cm.

The sustained-release pheromone preparations having respective pheromone substances of EGVM and VMB added were placed at 500 preparations/ha in a vineyard in Sicily in Italy on March 5 in Example 13. The sustained release pheromone preparations were placed separately with equal intervals in Plot 1 where insect pests were controlled, to release a necessary amount of the pheromone substances. The results showing a ratio of grape bunches damaged by the third generation and measured on August 26 are shown in Table 4.

A damaged bunch ratio in Plot 2 where no sustained-release pheromone preparation was placed, was also measured in Comparative Example 4.

It should be noted that the term "damaged bunch ratio" is used for estimating a mating disruption effect. Particularly in grapes, the damaged bunch ratio represented by the formula: {(number of damaged bunches)/(number of bunches checked)}×100 is used as one of estimate criteria.

TABLE 4

| | plot | damaged bunch ratio (%) by VMB | damaged bunch ratio (%) by EGVM |
|---|---|---|---|
| Example 13 | Plot 1 | 2.5 | 3.4 |
| Comp. Ex. 4 | Plot 2 | 20.2 | 10.4 |

In Example 13, VMB was controlled with the sustained release pheromone preparation having the pheromone substance of VMB added, and as a result, an average damaged bunch ratio by VMB was as good as 2.5%. In Comparative Example 4, VMB was controlled without a sustained release pheromone preparation having the pheromone substance of VMB added, and as a result, an average damaged bunch ratio by VMB was as high as 20.2%.

An average damaged bunch ratio by EGVM was 3.4% in the plot of Example 13, while an average damaged hunch ratio by EGVM was 10.4% in the plot of Comparative Example 4. Thus, the preparations exhibit a control effect also against EGVM.

The invention claimed is:

1. A sustained release pheromone preparation comprising:
    a first pheromone substance, and
    a first container having the first pheromone substance sealed therein and comprising a first polymer membrane made of an ethylene-vinyl acetate copolymer containing vinyl acetate units of from 0.5 to 10 wt %,
    wherein the first pheromone substance is lavandulyl senecioate, which is a pheromone substance of vine mealybug, and the lavandulyl senecioate can be released into the air through the first polymer membrane for 150 days or more.

2. The sustained release pheromone preparation according to claim 1, further comprising a second pheromone substance, and at least one second container having the second pheromone substance sealed therein and comprising a second polymer membrane.

3. The sustained release pheromone preparation according to claim 2, wherein the second pheromone substance is selected from the group consisting of lavandulyl senecioate, an aliphatic acetate having a carbon atom number of from 12 to 20 including a carbon atom number of its functional group, and an aliphatic aldehyde having a carbon atom number of from 12 to 20 including a carbon atom number of its functional group.

4. The sustained release pheromone preparation according to claim 3, wherein the second pheromone substance is (E,Z)-7,9-dodecadienyl acetate.

5. The sustained release pheromone preparation according to claim 2, wherein the second polymer membrane is selected from the group consisting of ethylene-vinyl acetate copolymers, polyolefins, vinyl-based polymers, polyesters, and biodegradable polymers.

6. The sustained release pheromone preparation according to claim 1, wherein each of the first container and, if any, the second container, is in form of a tube, a capsule, an ampoule or a bottle.

7. A method of controlling vine mealybug, comprising the step of:
    releasing, to a field, the lavandulyl senecioate from the sustained release pheromone preparation as claimed in claim 1.

8. A method of simultaneously controlling vine mealybug and European grapevine moth, comprising the step of:
    releasing, to a field, the lavandulyl senecioate and the (E,Z)-7,9-dodecadienyl acetate from the sustained release pheromone preparation as claimed in claim 4.

* * * * *